United States Patent [19]

Myers et al.

[11] Patent Number: 5,721,237
[45] Date of Patent: Feb. 24, 1998

[54] PROTEIN TYROSINE KINASE ARYL AND HETEROARYL QUINAZOLINE COMPOUNDS HAVING SELECTIVE INHIBITION OF HER-2 AUTOPHOSPHORYLATION PROPERTIES

[75] Inventors: Michael R. Myers, Reading; Alfred P. Spada, Lansdale; Martin P. Maguire, Mont Clare; Paul E. Persons, King of Prussia, all of Pa.

[73] Assignee: Rhone-Poulenc Rorer Pharmaceuticals Inc., Collegeville, Pa.

[21] Appl. No.: 469,147

[22] Filed: Jun. 6, 1995

Related U.S. Application Data

[63] Continuation-in-part of PCT/US94/14180, Dec. 8, 1994 and continuation-in-part of Ser. No. 166,199, Dec. 10, 1993, Pat. No. 5,480,883, which is a continuation-in-part of Ser. No. 988,515, filed as PCT/US92/03736, May 6, 1992, abandoned, which is a continuation-in-part of Ser. No. 698,420, May 10, 1991, abandoned.

[51] Int. Cl.$^6$ .............. A61K 31/505; C07D 403/04; C07D 235/02
[52] U.S. Cl. .............. 514/259; 514/255; 544/283; 544/284; 544/287; 544/293
[58] Field of Search .............. 544/283, 284, 544/287, 293; 514/255, 259

[56] References Cited

U.S. PATENT DOCUMENTS

| | | | |
|---|---|---|---|
| 3,715,358 | 2/1973 | Witzel et al. | 514/327 |
| 3,718,743 | 2/1973 | Shen et al. | 514/327 |
| 3,985,749 | 10/1976 | Foster | 544/293 |
| 4,322,420 | 3/1982 | Kobayashi et al. | 514/259 |
| 4,464,375 | 8/1984 | Kobayashi et al. | 514/259 |
| 4,465,686 | 8/1984 | Lesher et al. | 514/345 |
| 4,599,423 | 7/1986 | Lesher et al. | 546/300 |
| 4,661,499 | 4/1987 | Young et al. | 514/311 |
| 5,646,153 | 7/1997 | Spada et al. | 514/259 |

FOREIGN PATENT DOCUMENTS

| | | |
|---|---|---|
| 9331010 | 1/1993 | Australia . |
| 0 520 722 | 12/1992 | European Pat. Off. . |
| 1543560 | 4/1979 | United Kingdom . |
| WO 92/20642 | 11/1992 | WIPO . |

OTHER PUBLICATIONS

Tetrahedron, vol. 38, No. 22, pp. 3347–3354 (1982), Tamao et al.
Synthesis, pp. 564–565 (Jul. 1986), Yamamoto et al.
Chem. Pharm. Bull., vol. 30, No. 6, pp. 2003–2010 (1982), Yamamoto et al.
Heterocycles, vol. 23, No. 9, pp. 2375–2386 (1985), Ishikura et al.
J. Am. Chem. Soc., vol. 111, No. 3, pp. 877–891 (1989), Stern et al.
Chemical Abstract, vol. 84:164632t, p. 453 (1976), Yoshida.
Chemical Abstracts, vol. 103:123292z, p. 709 (1985), Barker et al.
Chemical Abstract, vol. 108:55860j, p. 704 (1988), Epling.
Beilstein–Band EIII/IV 21, p. 2436 (1978).
J.Heterocyclic Chem., vol. 20, pp. 1739–1740 (1983), Saeed et al.

*Primary Examiner*—Richard L. Raymond
*Attorney, Agent, or Firm*—Raymond S. Parker, III; James A. Nicholson; Martin F. Savitzky

[57] ABSTRACT

This invention relates to a method for the selective treatment of cell growth and differentiation characterized by activity of the human epidermal growth factor receptor type 2 (HER2). More specifically, this invention relates to the use of substituted or unsubstituted mono- or bi-cyclic aryl, heteroaryl, cycloalkyl or heterocycloalkyl compounds in selectively regulating cell growth. Pharmaceutical compositions useful for the selective treatment of cell growth and differentiation are also described.

13 Claims, No Drawings

1

PROTEIN TYROSINE KINASE ARYL AND HETEROARYL QUINAZOLINE COMPOUNDS HAVING SELECTIVE INHIBITION OF HER-2 AUTOPHOSPHORYLATION PROPERTIES

This application is a continuation-in-part application of PCT International Application Serial No. PCT/US94/14180 having International filing date of Dec. 8, 1994, and a CIP application of United States and U.S. Ser. No. 08/166,199, filed Dec. 10, 1993, now U.S. Pat. No. 5,480,893, which is a continuation-in-part application of U.S. Ser. No. 07/988,515, filed Dec. 10, 1992, now abandoned, which is a continuation-in-part application of U.S. Ser. No. 07/698,420, filed May 10, 1991, now abandoned, and PCT International Application Serial No. PCT/US92/03736 filed May 6, 1992.

BACKGROUND OF THE INVENTION

This invention relates to a method for the selective treatment of cell growth and differentiation characterized by activity of the human epidermal growth factor receptor type 2 (HER2). More specifically, this invention relates to the use of substituted or unsubstituted mono- or bi-cyclic aryl, heteroaryl, cycloalkyl or heterocycloalkyl compounds in selectively regulating cell growth.

Normal cellular reproduction is believed to be triggered by the exposure of the cellular substrate to one or more growth factors, examples of which are insulin, epidermal growth factor (EGF) and platelet-derived growth factor (PDGF). Such growth factor receptors are imbedded in and penetrate through the cellular membrane. The initiation of cellular reproduction is believed to occur when a growth factor binds to the corresponding receptor on the external surface of the cellular membrane. This growth factor-receptor binding alters the chemical characteristics of that portion of the receptor which exists within the cell and which functions as an enzyme to catalyze phosphorylation of either an intracellular substrate or the receptor itself, the latter being referred to as autophosphorylation. Examples of such phosphorylation enzymes include tyrosine kinases, which catalyze phosphorylation of tyrosine amino acid residues of substrate proteins.

Many disease states are characterized by the uncontrolled reproduction of cells. These disease states involve a variety of cell types and include disorders such as leukemia, cancer, psoriasis, inflammatory diseases, bone diseases, atherosclerosis and restenosis occuring subsequent to angioplastic procedures. The inhibition of tyrosine kinase is believed to have utility in the control of uncontrolled cellular reproduction, i.e., cellular proliferative disorders.

Initiation of autophosphorylation, i.e., phosphorylation of the growth factor receptor itself, and of the phosphorylation of a host of intracellular substrates are some of the biochemical events which are involved in mediator release mitogenesis and cell proliferation. Autophosphorylation of the insulin receptor and phosphorylation of substrate proteins by other receptors are the earliest identifiable biochemical hormonal responses.

Elimination of the protein tyrosine kinase (PTK) activity of the insulin receptor and of the epidermal growth factor (EGF) receptor by site-directed mutagenesis of the cellular genetic material which is responsible for generation of insulin and EGF results in the complete elimination of the receptor's biological activity. This is not particularly desirable because insulin is needed by the body to perform other biological functions which are not related to cell proliferation. Accordingly, compounds which inhibit the PTK portion of the EGF and/or PDGF receptor at concentrations less than the concentrations needed to inhibit the PTK portion of the insulin receptor could provide valuable agents for selective treatment of cell proliferation disorders.

REPORTED DEVELOPMENTS

It is generally accepted that the protein tyrosine kinase (PTK) activity associated to growth factor receptors is essential for ligand-induced biological responses, such as cell growth and differentiation. J. M. Bishop, (1985) *Cell*, 42:23–38 and T. Hunter (1987) *Cell*, 50:823–829 have reported evidence for abnormal cell growth and morphological transformation via tyrosine phosphorylation, growth factor receptors represent a bonafide oncogene family. Among these oncogene products, is the human epidermal growth factor receptor type 2 (HER2; c-erbB-2). Carpenter et al. (1987) *Annu. Rev. Biochem.*,56:881—and Gill et al. (1987) *Mol. Cell. Endocrinol.*, 51:169—have reported that the c-erbB-1 gene encodes a 170 kDa transmembrane glycoprotein. The HER2 gene is the human homolog of the rat protooncogene neu as reported by C. I. Bargmann, M. C. Hung and R. A. Weinberg (1986) *Nature*, 319:226–229 and its product is a 185-kDa transmembrane cell-surface glycoprotein, so called $p185^{HER2}$ as reported by Coussens et al. (1985) *Science*, 230:1132–1139 and Yamamoto et al. (1986) *Nature*, 319:230–234. This receptor harbors an intrinsic tyrosine-specific kinase activity which is capable of catalyzing autophosphorylation reaction as well as mediating endogenous substrate phosphorylation upon binding of their cognate ligands on the receptor extracellular domains.

The unaltered HER2 gene has been found amplified in various human tumors. In addition, a correlation between the elevated levels of $p\ 185^{HER2}$ expression and poor prognosis or short survival time has been established in patients with several cancer types. Given that the use of antibodies raised against $p185^{HER2}$ (that block receptor functions) results in a growth arrest of tumor-derived cell lines and anti-tumor effect in mice, strategy in which chemically-designed agents that selectively inhibit $p185^{HER2}$-associated PTK are valuable in cancer therapy. It is now widely documented that numerous naturally occurring and synthetic analogues of PTK inhibitors have been systematically evaluated for their potential anti-tumor efficacy as reported by C. Workman, V. G. Brunton and D. J. Robins (1992) in *seminars in Cancer Biology*, 369–381 and C. Wasylyk, A. Gutman, R. Nicholson and B. Wasylyk (1991) *EMBO J.*, 10:1127–1134.

Applicants describe herein the identification and characterization of a series of quinazolin derivatives—which are tyrosine kinase inhibitors exhibiting selectivity for $p185^{HER2}$. In particular, Applicants demonstrate the requirement of tyrosine kinase activity associated to HER2 gene product for maintaining transformed cell phenotype induced by overexpression of $p185^{HER2}$.

SUMMARY OF THE INVENTION

In accordance with the present invention, there is provided a method for the selective treatment of cell growth and differentiation characterized by activity of the human epidermal growth factor receptor type 2 (HER2) comprising administering to a patient in need of such treatment an HER2 receptor inhibiting effective amount of a quinazoline compound described in this invention.

Another aspect of the present invention relates to pharmaceutical compositions for selectively treating cell growth and differentiation characterized by activity of the human .epidermal growth factor receptor type 2 (HER2) comprising, in admixture with a pharmaceutically acceptable carrier, a pharmaceutically effective amount of a compound of the aforementioned type.

A further aspect of this invention comprises novel compounds useful in the practice of the present method.

With respect to the aspects of this invention, the compounds described by Formula I below constitute a class of the aforementioned quinazoline compounds for use in the practice of the present invention:

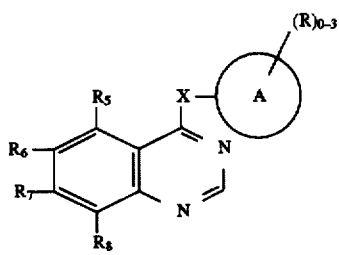

Formula I wherein

A is a substituted or unsubstituted mono- or hi-cyclic aryl, heteroaryl, cycloalkyl or heterocycloalkyl ring system of about 5 to about 12 atoms and where the substituents may be located at any appropriate position of the ring system and are described by R;

X is a bond, O, S, SO, $SO_2$, $OCH_2$, $CR_4=CR_4$, $C\equiv C$, $NR_4$ or $NR_4CH_2$;

R independently includes hydrogen, alkyl, phenyl, halophenyl, aralkyl, hydroxy, alkoxy, aryloxy, acyloxy, halo, haloalkyl, amino, mono- and di-alkylamino, acylamino, carboxy, amido, mono- and di-alkylamido, alkylthio, alkylsulfinyl, and alkylsulfonyl.

$R_4$ is hydrogen, alkyl or aralkyl; and $R_5$, $R_6$, $R_7$ and $R_8$ are independently hydrogen, alkoxy or aralkoxy; or a pharmaceutically acceptable salt thereof.

DETAILED DESCRIPTION AND PREFERRED EMBODIMENTS

As employed above and throughout this disclosure, the following terms, unless otherwise indicated, shall be understood to have the following meanings:

"Monocyclic aryl" or "monocyclic heteroaryl" means a carbocyclic or heterocyclic aromatic ring. Preferred rings include phenyl, pyrrolyl, thienyl, furyl, thiazolyl, imidazolyl, pyrazolyl, pyridyl, pyrazinyl, pyrimidinyl, pyridazinyl, isothiazolyl, isoxazolyl and oxazolyl.

"Bicyclic aryl" or "bicyclic heteroaryl" means a bicyclic ring system composed of two fused rings at least one of which is a carbocyclic or heterocyclic aromatic ring. Preferred rings include substituted and unsubstituted naphthyl, tetralinyl, 1,2,3,4-tetrahydroquinolinyl, benzofuryl, benzothienyl, indolyl, indolinyl, 1,3-benzodioxolyl, benzodioxanyl, quinolinyl, tetrahydroquinolinyl, isoquinolinyl, quinazolinyl and quinoxalinyl.

"Monocyclic cycloalkyl" means a cyclic aliphatic ring comprising from about four to about seven carbon atoms such as substituted and unsubstituted cyclopentyl, cyclohexyl and cycloheptyl.

"Bicyclic cycloalkyl" means a saturated bicyclic ring system composed of two fused aliphatic rings comprising about 8 to about 12 carbon atoms such as substituted and unsubstituteddecalinyl.

"Monocyclic heterocycloalkyl" means a saturated cyclic aliphatic ring comprising from about four to about seven atoms and includes 1–2 hetero atoms selected from N, O and S provided said hetero atoms are not vicinal oxygen and/or sulfur atoms such as substituted and unsubstituted piperdinyl, piperazinyl and morpholinyl.

"Bicyclic heterocycloalkyl" means a saturated bicyclic ring system comprising two fused aliphatic rings of about 8 to about 12 atoms and includes 1–3 hetero atoms selected from N, O and S provided said hetero atoms are not vicinal oxygen and/or sulfur atoms such as substituted and unsubstituted decahydroquinolinyl.

"Alkyl" means a saturated aliphatic hydrocarbon, either branched- or straight-chained. Preferred alkyl is "lower-alkyl" having about 1 to about 6 carbon atoms. Examples of alkyl include methyl, ethyl, n-propyl, isopropyl, butyl, sec-butyl, t-butyl, amyl and hexyl.

"Alkoxy" refers to an alkyl-O-group. Preferred alkoxy groups include methoxy, ethoxy, propoxy and butoxy.

"Aryloxy" refers to an aryl-O-group. The preferred aryloxy group is phenoxy.

"Aralkyl" means an alkyl group substituted by an aryl radical. The preferred aralkyl groups are benzyl or phenethyl.

The preferred aralkoxy groups are benzyloxy and phenethoxy.

The preferred acyloxy groups are acetoxy and benzyloxy;

"Halo" means halogen. Preferred halogens include chloride, bromide and fluoride.

The preferred haloalkyl groups are mono-, di- and trifluoromethyl.

More specifically, the preferred A monocyclic aryl or heteroaryl rings include substituted or unsubstituted phenyl, pyrrolyl, thienyl, furyl, thiazolyl, imidazolyl, pyrazolyl, pyridyl, pyrazinyl, pyrimidinyl, pyridazinyl, isothiazolyl, isoxazolyl and oxazolyl.

The preferred A bicyclic aryl or heteroaryl rings include substituted and unsubstituted naphthyl, tetralinyl, 1,2,3,4-tetrahydroquinolinyl, benzofuryl, benzothienyl, indolyl, indolinyl, 1,3-benzodioxolyl, benzodioxanyl, quinolinyl, tetrahydroquinolinyl, isoquinolinyl, quinazolinyl and quinoxalinyl.

The preferred A monocyclic cycloalkyl or heterocycloalkyl rings include substituted and unsubstituted cyclopentyl, cyclohexyl, cycloheptyl, decalinyl, piperdinyl, piperazinyl, morpholinyl or decahydroquinolinyl.

The preferred A bicyclic cycloalkyl or heterocycloalkyl rings include substituted and unsubstituted decalinyl or decahydroquinolinyl.

The more preferred compounds are those where:
A is substituted and unsubstituted phenyl, pyridyl, thienyl, furyl, pyrazolyl, naphthyl, tetralinyl, 1,2,3,4-tetrahydroquinolinyl, indolyl, indolinyl, quinolinyl, tetrahydroquinolinyl, cyclohexyl, piperdinyl or piperazinyl;

X is a bond, O, S, or $NR_4$;

R is hydrogen, alkyl, alkoxy, halo, haloalkyl, alkylthio, alkylsulfinyl, alkylsulfonyl, phenyl and aralkyl;

$R_4$ is hydrogen, alkyl or aralkyl; and $R_5$, $R_6$, $R_7$, and $R_8$ are independently hydrogen or alkoxy.

The most preferred compounds are those where:
A is substituted and unsubstituted phenyl, naphthyl or indolyl;

X is a bond;

R is hydrogen, methoxy, ethoxy, chloro, trifluoromethyl, methylsulfonyl, phenyl and benzyl;

$R_4$ is hydrogen, methyl or benzyl; and $R_5$, $R_6$, $R_7$, and $R_8$ are independently hydrogen or methoxy.

Compounds within the scope of this invention are selective tyrosine kinase inhibitors of the human epidermal growth factor receptor type 2 (HER2). It is believed that therapeutically useful PTK inhibiting compounds have a specific tyrosine kinase activity which is capable of catalyzing autophosphorylation. In addition these compounds should inhibit growth factor-induced cell proliferation. Compounds meeting these criteria are of considerable value and are particularly useful in the practice of the present invention. Compounds exhibiting selectivity for the above receptor are described herein.

The compounds of this invention may be useful in the form of the free base, in the form of salts and as a hydrate. All forms are within the scope of the invention. Acid addition salts may be formed and are simply a more convenient form for use; and in practice, use of the salt form inherently amounts to use of the base form. The acids which can be used to prepare the acid addition salts include preferably those which produce, when combined with the free base, pharmaceutically acceptable salts, that is, salts whose anions are non-toxic to the animal organism in pharmaceutical doses of the salts, so that the beneficial properties inherent in the free base are not vitiated by side effects ascribable to the anions. Although pharmaceutically acceptable salts of said basic compound are preferred, all acid addition salts are useful as sources of the free base form even if the particular salt per se is desired only as an intermediate product as, for example, when the salt is formed only for purposes of purification and identification, or when it is used as an intermediate in preparing a pharmaceutically acceptable salt by ion exchange procedures.

Pharmaceutically acceptable salts within the scope of the invention include those derived from the following acids: mineral acids such as hydrochloric acid, sulfuric acid, phosphoric acid and sulfamic acid; and organic acids such as acetic acid, citric acid, lactic acid, tartaric acid, malonic acid, methanesulfonic acid, ethanesulfonic acid, benzenesulfonic acid, p-toluenesulfonic acid, cyclohexylsulfamic acid, quinic acid, and the like.

The corresponding acid addition salts comprise the following: hydrochloride, sulfate, phosphate, sulfamate, acetate, citrate, lactate, tartrate, methanesulfonate, ethanesulfonate, benzenesulfonate, p-toluenesulfonate, cyclohexylsulfamate and quinate, respectively.

The acid addition salts of the compounds of this invention are prepared either by dissolving the free base in aqueous or aqueous-alcohol solution or other suitable solvents containing the appropriate acid and isolating the salt by evaporating the solution, or by reacting the free base and acid in an organic solvent, in which case the salt separates directly or can be obtained by concentration of the solution.

The compounds of this invention may be prepared by employing procedures known in the literature starting from known compounds or readily prepared intermediates. Exemplary general procedures follow.

In general the compounds useful for the method for the selective treatment of cell growth and differentiation characterized by activity of the human epidermal growth factor receptor type 2 may be prepared by the coupling reaction of a palladium catalyzed aryl or heteroarylstannane with an aryl or heteroarylhalide or triflate.

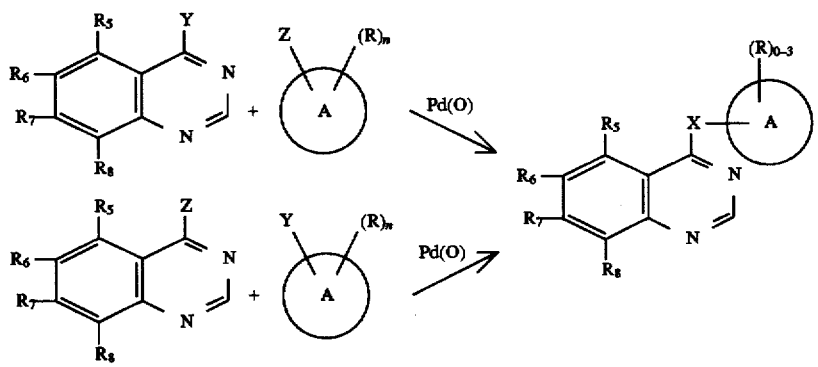

where Y is halogen or triflate and Z is trialkylstannane and R is as previously described.

The 4-haloquinazoline starting materials are prepared in the classical way using anthranilic acid derivatives and formamide at reflux to provide the intermediate quinazolinones. Subsequent treatment with $POCl_3$ at about 110° C. for about two hours provides the chloroquinazolines. The final products are prepared via a condensation with the appropriate aniline derivative in a polar solvent such as ethanol. In the case of the phenoxy or thiophenoxy derivatives, the metal salt (preferably Na) is prepared and refluxed for several hours with the appropriate haloquinazoline in a solvent such as THF.

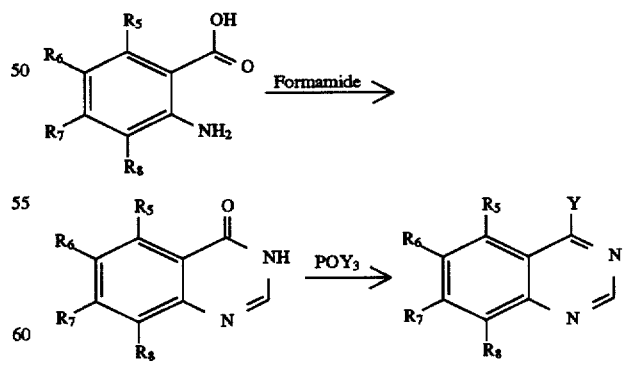

The aryl and heteroarylstannanes may be prepared from the corresponding halide (preferably bromide or iodide) by conversion to the aryllithium by reaction with t-butyllithium at decreased temperatures, preferably about −78° C. followed by reaction with a halotrialkylstannane.

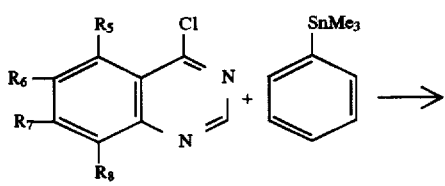

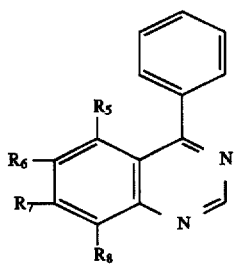

Of course these products may also be prepared in the reverse manner using the aryl or heteroarylhalides with the the corresponding stannane.

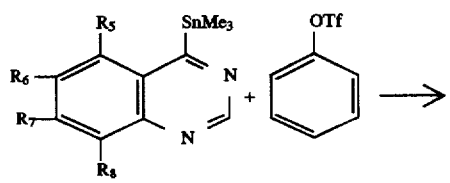

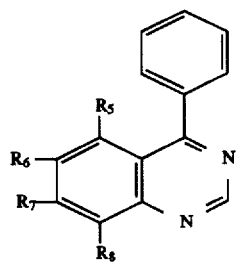

The quinazoline stannanes intermediates may be prepared by the action of trimethyltin sodium on aryl halides as described in Chem. Pharm. Bull. 1982, 30, 1731–1737.

The preparation of the compounds useful in this invention are described in Applicants' copending applications PCT/US94/14180 having International filing date Dec. 8, 1994 and designating the United States as a contracting state, U.S. Ser. No. 08/166,199, filed Dec. 10, 1993, now U.S. Pat. No. 5,480,883 and U.S. Ser. No. 08/229,886, filed Apr. 19, 1994 all of which this application claims priority. PCT/US94/14180, U.S. Ser. No. 08/166,199 and U.S. Ser. No. 08/229,886 are hereby incorporated herein by reference.

Further, the following examples are representative of the processes used to synthesis the compounds of this invention.

The below examples and those described in PCT/US94/14180 and U.S. Ser. No. 08/166,199 may be followed to prepare any of the desired compounds of this invention. A representative list of compounds which may be prepared is shown below.

EXAMPLE 1

4-(3-Chlorophenoxy)-6,7-dimethoxyquinazoline

THF (5 ml) and NaH (60% disp in oil, approx. 28 mg) is added to a dry flask maintained under inert atmosphere at room temperature. 3-Chlorophenol (0.09 g) is added as a soln. in THF (1 mL) and stirring is continued until the solution became clear. 4-Chloro-6,7-dimethoxyquinazoline is added all at once (as the solid) and stirring was maintained overnight at RT. The solution is partitioned between $CH_2Cl_2$ and 5% NaOH. The organic layer is washed with brine, dried ($Na_2SO_4$) and concentrated. Flash column chromatography (40% EtOAc/Hex) provided the pure compound. An analytical sample is obtained by recrystallization from EtOAc/Hex to provide 4-(3-chlorophenoxy)-6,7-dimethoxyquinazoline (0.05 g), white needles, m.p. 152°–153° C.

EXAMPLE 2

4-(1-methylsulphonylindol-3-yl)-6,7-dimethoxyquinazoline

Step A N-methylsulfonyl-3-trimethylstannylindole

A solution of 5 g (15.57 mmol) of N-methylsulfonyl-3-iodoindole (5.1 g; 15.57 mmol) of hexamethylditin and 0.89 g (0.78 mmol) of Pd ($PPh_3$)$_4$ in 75 mL of dry toluene is flushed thoroughly with nitrogen and heated to 90° C. for 4 hours. The mixture is then evaporated and chromatographed on silica gel (eluting with hexane and then with 10% ethyl acetate/hexane to give N-methylsulfonyl-3-trimethylstannylindole which is used directly in the next step.

Step B 4-(1-methylsulphonylindol-3-yl)-6,7-dimethoxyquinazoline

A solution of 1.33 g (4.01 mmol) of N-methylsulfonyl-3-trimethylstannylindole, 750 mg (3.34 mmol) of 4-chloro-6,7-dimethoxyquinazoline and 0.19 g (5 mol % 0.16 mmol) of Pd ($PPh_3$)$_4$ in 10 ml of dry dimethylformamide is flushed thoroughly with nitrogen and heated to 90° C. for 12 hours. The reaction mixture is diluted with methylene chloride washed with 10% ammonium hydroxide and stirred vigorously and then washed with water and the combined organics are washed with brine (75 mL), dried ($MgSO_4$) and evaporated to dryness. Recrystallization from ethyl acetate yields 4-(1-methylsulphonylindol-3-yl)-6,7-dimethoxyquinazoline (m.p.>220° C.).

The above examples may be followed to prepare any of the desired compounds of this invention. A representative list of compounds which may be prepared are shown below.

6,7-dimethoxy-4-naphthalen-2-ylethynylquinazoline, m.p. 158°–161° C.

4-(4-hydroxyphenyl)-6,7-dimethoxyquinazolinehydrochloride, m.p.>270° C. (dec)

4-(naphthalen-1-yl)-6,7-dimethoxyquinazoline, m.p. 144°–147° C.

4-(naphthalen-2-yl)-6,7-dimethoxyquinazoline, m.p. 115°–118° C.

4-phenylacetylenyl-6,7-dimethoxyquinazoline, m.p. 146°–148° C.

4-(3-fluoro-4-methoxyphenyl)-6,7-dimethoxyquinazoline, m.p. 207°–210° C.

4-(3-phenylphenyl)-6,7-dimethoxyquinazoline, m.p. 160°–163° C.

4-(2-phenylethylenyl)-6,7-dimethoxyquinazoline, m.p. 168°–169° C.

4-(2-methoxypyridin-5-yl)-6,7-dimethoxyquinazoline, m.p. 175°–176° C.

4-(1-benzylindol-3-yl)-6,7-dimethoxyquinazoline, m.p. 148°–150° C.

4-(indol-3-yl)-6,7-dimethoxyquinazoline, m.p.>240° C. (dec)

4-(1-methylindol-3-yl)-6,7-dimethoxyquinazoline hydrochloride, m.p.>230° C. (dec)

4-(1-methylsulphonylindol-3-yl)-6,7-dimethoxyquinazoline, m.p.>220° C. (dec)

4-(4-phenylpiperidin-1-yl)-6,7-dimethoxyquinazoline, m.p. 150°–151° C.

4-[4-(3-chlorophenyl)piperazin-1-yl]-6,7-dimethoxyquinazoline, m.p. 155°–156° C.

4-(N-methyl-3,4,5-trimethoxyanilino)-6,7-dimethoxyquinazoline, m.p. 149°–151° C.

(+–)-4-(2-methyl-1,2,3,4-tetrahydroquinolin-1-yl)-6,7-dimethoxyquinazoline hydrochloride, m.p. 198°–201° C. (dec)

4-(1,2,3,4-tetrahydroquinolin-1-yl)-6,7-dimethoxyquinazoline hydrochloride, m.p. 195°–197° C. (dec)

4-(5,6,7,8-tetrahydronaphthalen-1-yl)amino-6,7-dimethoxyquinazoline hydrochloride, m.p. 219°–222° C.

4-(3,6-dioxananilino)-6,7-dimethoxyquinazoline, m.p. 267°–269° C. (dec)

4-phenylacetylenyl-6,7-dimethoxyquinazoline, m.p. 146°–148° C.

4-(indol-1-yl)-6,7-dimethoxyquinazoline, m.p. 166°–167° C.

-(N-methyl-4-methoxyanilino)-6,7-dimethoxyquinazoline hydrochloride, m.p. 202°–205° C.

4-(N-methyl-4-chloroanilino)-6,7-dimethoxyquinazoline hydrochloride, m.p. 220°–222° C.

4-(2,3-dihydroindol-1-yl)-6,7-dimethoxyquinazoline hydrochloride, m.p. 226°–229° C. (dec)

N-(6,7-dimethoxyquinazolin-4-yl)-N-methyl-N-(3-trifluoromethylphenyl)amine hydrochloride, m.p. 240°–243° C.

N-(3-chlorophenyl)-N-(6,7-dimethoxyquinazolin-4-yl)-N-methylamine hydrochloride, m.p. 235°–237° C.

N-(3-chlorophenyl)-N-(quinazolin-4-yl)-N-methyl-amine hydrochloride, m.p. 233°–235° C.

6,7-dimethoxy-4-naphthalen-1-yl-ethynylquinazoline, m.p. 175°–177° C.

4-(thien-3-yl)-6,7-dimethoxyquinazoline, m.p. 148.5°–151.5° C.

4-benzyl-6,7-dimethoxyquinazoline, m.p. 122.5°–125° C.

(6,7-dimethoxyquinazolin-4-yl)-5-indazolylamine hydrochloride, m.p. 261°–263° C. (dec)

N-(6,7-dimethoxyquinazolin-4-yl)-N-phenyl-N-ethylamine hydrochloride, m.p. 227°–230° C. (dec)

N-benzyl-N-(6,7-dimethoxyquinazolin-4-yl)-N-phenylamine hydrochloride, m.p. 269°–271° C.

N-(6-chloroquinazolin-4-yl)-N-methyl-N-phenylamine, m.p. 106°–108° C.

N-(3-chloro-phenyl)-N-(6,7-dimethoxyquinazolin-4-yl)-N-ethylamine hydrochloride, m.p. 261°–263° C.

N-(6,7-dimethoxyquinazolin-4-yl)-N-methyl-N-p-tolylamine hydrochloride, m.p. 230°–234° C. (dec)

N-benzyl-N-(6,7-dimethoxyquinazolin-4-yl)amine, m.p. 220°–225° C.

N-(4-methoxybenzyl)-N-(6,7-dimethoxyquinazolin-4-yl)amine, m.p. 194°–198° C.

N-(3,5-dimethoxybenzyl)-N-(6,7-dimethoxyquinazolin-4-yl)amine hydrochloride, m.p. 265°–269° C.

4-(3,4,5-trimethoxyphenoxy)-6,7-dimethoxyquinazoline, m.p. 228°–232° C.

N-(quinazolin-4-yl)-N-phenyl-N-methylamine hydrochloride, m.p. 242°–246° C. (dec)

N-(6,7-dimethoxyquinazolin-4-yl)-N-(4-morpholin-4-ylphenyl)amine hydrochloride, m.p. 231°–235° C. (dec)

4-(3-methoxythiophenoxy)-6,7-dimethoxyquinazoline, m.p. 139.5°–141.5° C.

4-[N-(5-indanyl)amino]-6,7-dimethoxyquinazoline hydrochloride, m.p. 244°–246° C. (dec)

4-(3-chlorothiophenoxy)-6,7-dimethoxyquinazoline, m.p. 152°–153.5° C.

4-(3-aminopyrazolyl)-6,7-dimethoxyquinazoline hydrochloride, m.p. 262°–264° C. (dec)

4-(1,4-benzodioxan-6-ylamino)-6,7-dimethoxyquinazoline hydrochloride, m.p. 267°–269° C. (dec)

6,7-dimethoxy-4-(α-naphthylamino)quinazoline hydrochloride, m.p.>250° C.

6,7-dimethoxy-4-(β-naphthylamino)quinazoline hydrochloride, m.p.>250° C.

4-(cyclohexylanilino)-6,7-dimethoxyquinazoline, m.p. 239°–244° C.

4-(3,4,5-trimethoxyanilino)-6,7-dimethoxyquinazoline hydrochloride, m.p. 260°–265° C.

6,7-dimethoxy-4-(N-methylanilino)quinazoline hydrochloride, m.p.>230° C.

4-(3-chlorophenoxy)-6,7-dimethoxyquinazoline, m.p. 152°–153° C.

6,7-dimethoxy-4-(1-naphthylthio)-quinazoline, m.p. 174.5°–176.5° C.

6,7-dimethoxy-4-(2-naphthylthio)-quinazoline, m.p. 178°–179° C.

6,7-dimethoxy-4-(1-naphthyloxy)-quinazoline, m.p. 214°–215.5° C.

6,7-dimethoxy-4-(2-naphthyloxy)-quinazoline, m.p. 169°–170° C.

N-(6,7-dimethoxy-quinolazolin-4-yl)-N-(naphth-2-yl)-N-ethylamine hydrochloride, m.p. 236°–239° C. (dec)

6,7-dimethoxy-4-(naphthalene-2-sulfinyl)quinazoline, m.p. 182.5°–185° C.

6,7-dimethoxy-4-(naphthalene-2-sulfonyl)quinazoline 4-(3-chloroanilino)-6,7-dimethylquinazoline hydrochloride, m.p. 271°–274° C.

4-(3,5-dimethylanilino)-6,7-dimethylquinazoline hydrochloride, m.p.>275° C.

4-(N-methyl-4-methylanilino)-6,7-dimethylquinazoline hydrochloride, m.p. 235°–238° C.

6,7-dimethyl-4-(1-naphthylamino)quinazoline hydrochloride, m.p. 244°–247° C.

6,7-dimethyl-4-(7-trifluoromethyl-3,4-dihydro-2H-quinolin-1-yl)quinazoline hydrochloride, m.p. 240° C.

4-(N-methyl-3-methylanilino)-6,7-dimethylquinazoline hydrochloride, m.p. 205°–207° C.

4-(3-chlorophenylthio)-6,7-dimethylquinazoline hydrochloride, m.p. 197°–202° C.

4-(1-naphthylthio)-6,7-dimethylquinazoline hydrochloride, m.p. 204°–209° C.

4-(3,4-dimethoxyphenylthio)quinazoline, m.p. 115°–117° C.

Preparation of Pharmaceutical Compositions and Pharmacological Test Section

To determine the effectiveness of compounds of this invention, the pharmacological tests described below, which are accepted in the art and recognized to correlate with pharmacological activity in mammals, are utilized. Compounds within the scope of this invention have been subjected to these various tests, and the results obtained are believed to correlate to useful inhibition of growth factor-induced cell proliferation. The below described tests are useful in determining the inhibition of the compounds of this invention.

Experimental Procedures

Materials

The test material was dissolved extemporaneously in DMSO to make up stock solutions which were subsequently diluted in culture medium to reach the desired compound concentrations (vehicle final concentration of 0.1%). The materials used are as follows: Dulbecco's Modified Eagle Medium (DMEM), RPMI 1640, fetal calf serum (FCS), and Penicillin-Streptomycin solution (10,000 IU/ml penicillin and 10.0001 µg/ml streptomycin), were from GIBCO BRL. 3-(4, 5-dimethylthiazol-2 yl)-2, 5-diphenyltetrazolium bromide (MTT), and geneticin were from Sigma. Radiolabeled [$\gamma$-$^{32}$P]ATP (cat#NEG002H; 3,000 Ci/mmol), was purchased from NEN. Anti-c neu antibodies (Ab-5; cat#OP39) were from Oncogene Science. Mouse monoclonal anti-phosphotyrosine antibodies (monoclonal IgG2bk) were from UBI and horseradish peroxidase-conjugated rabbit anti-mouse IgG were from Nordic Immunological Laboratories. Stromelysin-CAT plasmid DNA construct, consisting of the chloramphenicol acetyl transferase cDNA under the control of the stromelysin promoter fragment −1100/+8 was prepared by the procedure of C. Wasylyk, A. Gutman, R. Nicholson and B. Wasylyk, (1991) *EMBO J.*, 10:A127-A134. All other chemicals were of the best quality available.

Cell Lines and Cell Culture

Mouse embryo fibroblasts (NIH3T3), human epidermoid (A431) carcinoma cell line, and breast (SK-BR-3) and ovary (SK-OV-3) adenocarcinoma cell lines, human lung (A549), and breast (BT474 and BT20) carcinoma cell lines were purchased from the ATCC. NIH3T3 cells transfected with HER2 construct and overexpressing p185$^{HER2}$, NIH/HER2 were prepared according to R. M. Hudziak, J. Schlessinger and A. Ullrich (1987) *Proc. Natl. Acad. Sci. USA*, 84:7159–7163. NIH/Ha-Ras cell line was established by transforming NIH3T3 cells with $^{val2}$Ha-ras according to I. Barlat, F. Schweighoffer, M. C. Chevalier-Multon, M. Duchesne, I. Faith, D. Landais, M. Jacquet and B. Tocqu é(1993) *Oncogene*, 8:215–218. NIH3T3 cells transfected with activated v-src containing mutation Y527F (NIH/v-Src) were obtained brom Dr. B. Wasylyk. HIR3.5 (NIH/IR) cell line represents NIH3T3 cells overexpressing the human insulin receptor and was provided by Dr. J. Whitaker. All cell lines were cultured at 37° C. in a $CO_2$ incubator (5% $CO_2$/95% humidified air atomosphere) in medium supplemented with 10% FCS and 1% penicillinstreptomycin solution. Unless specified in the text, the culture medium was changed every other day.

In Vitro p185$^{HER2}$ Autophosphorylation Assay

ER22 or A431, and NIH/HER2 cell lines were used as sources for p185$^{Her2}$. Subconfluent cell monolayers were lyzed at 4° C. for 10 min in HNEG buffer (HNEG: 50 mM Hepes buffer, pH 7.5, 150 mM NaCl, 1 mM EDTA and 10% Glycerol)containing 1% Triton X-100 and 1 mM PMSF. Cell lysates were then diluted with HNEG buffer containing 0.1% Triton X-100 and 1% BSA (lysis buffer), and cell extracts were clarified by centrifugation at 12,000. g for 5 min. Autophosphorylation assays were preformed as described by S. M. Smyth, I. Stefanova, F. Hartman, I. D. Horak, N. Osherov, A. Levitzki, and T. R. Burke (1993) *J. Med. Chem.*, 36:3010–3014. Briefly, 96 well U-bottom plastic plates were coated at 37° C. for 2 h with 100 µl of goat anti-mouse immunoglobulin (Biosys) at a concentration of 10 µg/ml. After several washes with PBS contqaining 0.05% Tween, 100 µl of anti-c-neu antibodies were incubated for 2 h at 37° C. (both antibodies were used at 1 µ/ml). Unoccupied binding sites were blocked by incubation for 1 h at 37° C. with 2% BSA in PBS. Cell lysates were incubated in coated wells for 1 h at 4° C. After several washes with lysis buffer autophosphorylation assay was performed directly in the wells in 25 mM Hepes buffer, pH 7.4, containing 2 mM $MnCl_2$, 0.1% Triton and 5 µCi [$\gamma$-$^{32}$P]ATP for 20 min at room temperature in the absense or the presence of Applicants' compounds. Phosphorylation reaction was quenched by adding Laemmli's sample buffer prepared according to U. K. Laemmli (1970)(*Nature*, 225:680–685 and [$^{32}$P]-labled receptors were analyzed by SDS-PAGE on 4–12% polyacrylamide gradient gels. Phosphorylation intensities were estimated by scanning the dried gels on an Instant Imager (Packard).

Intact Cell Tyrosine Phosphorylation

Content cell monolayers were serum-starved overnight after which they were incubated with the indicated compound concentrations for 2 h. Medium was then aspirated and cells were quenched by adding Laemmli's SDS-sample buffer directly on cell monolayers. Samples were then treated at 100° C. for 5 min before being tested for phosphotrosine-containing proteins. Proteins were fractionated by SDS-Page on 4–20% polyacrylamide gradient gels, after which proteins were electrophoretically transferred to polyvinylidene difluoride membranes (PVDF membrane, PolyScreen, NEN). Immunological detection of phosphotyrosine-containing proteins was performed using a mouse monoclonal anti-phosphotyrosine antibody. Blots were developed by the Enhanced ChemiLuminescence method (ECL, NEN) employing horseradish peroxidaseconjugated rabbit anti-mouse IgG.

Cell Proliferation

Cells were seeded onto 24 well cell culture plates at about 20,000 cells per well. Cells were allowed to adhere to plastic for 8 h in 1 ml culture medium, after which cells were cultured in the presence of various concentrations of compounds for 72–96 h. Following the indicated incubation times, cell number per well was estimated. As an assay of relative viable cell number, mitochondrial reduction of MTT was used following the procedure of M. C. Alley, D. A. Scudiero, A. Monks, M. L. Hursey, M. J. Czerwinski, D. L. Fine, B. J. Abbot, J. G. Mayo, R. H. Shoemaker and M. R. Boyd (1988) *Cancer Res.* 48:589–601. Briefly, 100 µl of a 5 mg/ml solution of MTT in phosphate-buffered saline was added to each well, and plates were incubated for 4 h at 37° C. in a $CO_2$ incubator. 650 µl of medium was then removed and replaced by 750 µl of an isopropyl alcohol/HC1 (1N) solution (25:1) in order to dissolve the dark purple crystals of formazan formed in the mitochondria of living cells. After incubation for 5–10 min at room temperature under agitation, 200-µl aliquots from each well were transfered to 96-well cell culture plates, and since the extent of obtained bluish color was directly proportional to cell number, this was estimated by spectrophotometry at 590 nm in a microplate autoreader.

Anchorage-Independent Cell Growth

Anchorage-independent cell growth was investigated by examining the colony-forming capability of the considered cells suspended in soft-agar. Experiments were performed using 50-mm diameter cell culture dishes. A 4-ml cell-free feeder underlayer consisted of 0.5% agar in medium supplemented with 10% FCS and the indicated concentrations of compounds. The 4-ml overlayer contains about 10,000 cells in 0.3% agar in medium supplemented with 10% FCS and the corresponding concentrations of compounds. After incubation for 2 weeks at 37° C., the number of colonies was determined.

Cell Transfaction and CAT Assay

Stromelysin-CAT plasmid DNA construct (STRM-CAT) was introduced into cells by transfaction using the lipofectAMINEreagent. Briefly, 50–70% confluent culture dishes (3.5-cm) of cells were exposed to 1 µg of plasmid DNA and 10 μg of lipofectAMINE reagent in 1 ml of serum-free DMEM for 4 h at 37° C. Cells were then incubated for 36 h at 37° C. with DMEM supplemented with 0.5% FCS and the indicated amounts of compounds. Cells were detached off the plates by incubation with PBS containing 3 mM EDTA and pelleted by centrifugation for 5 min at 1,500 rpm. Cells were resuspended in 0.25 M Tris/HCl buffer, pH 7.8 and were subjected to repeated freeze-thawing cycles. Cell extracts were heated to 65° C. for 15 min and, after cooling, were microfuged for 15 min at 14,000 rpm. Supernatants were assayed for CAT activity following the procedure of J. R. Neumann, C. A. Morency and K. O. Russian (1987) *BioTechniques*, 5:444–447.

Compounds within the scope of this invention exhibit significant specific activity as protein tyrosine kinase inhibitors and possess therapeutic value for inhibiting growth factor-induced cell proliferation Further, compounds of this invention are specific inhibitors of the human epidermal growth factor receptor type 2 and are therefore useful for treating cell growth and differentiation.

The following table shows examples of representative compounds of this invention and their test results as determined by the above inhibition of the human epidermal growth factor receptor type 2. The results obtained by the above experimental methods evidence the useful HER2 receptor protein tyrosine kinase inhibition properties of compounds within the scope of the present invention and possess therapeutic value in the regulation of abnormal cell growth.

| A-(R)₀₋₃ | X | R₅ | R₆ | R₇ | R₈ | HER-2 |
|---|---|---|---|---|---|---|
| N-methylindol-3-yl | bond | H | OCH₃ | OCH₃ | H | 20% at 5 μM |
| indol-3-yl | bond | H | OCH₃ | OCH₃ | H | 10% at 5 μM |
| 1-benzylindol-3-yl | bond | H | OCH₃ | OCH₃ | H | 0.5–1 μM |
| 1,2,3,4-tetrahydroquinolin-6-yl | bond | H | OCH₃ | OCH₃ | H | 10% at 5 μM |

The compounds of the present invention can be administered to a mammalian host in a variety of forms adapted to the chosen route of administration, i.e., orally, or parenterally. Parenteral administration in this respect includes administration by the following routes: intravenous, intramuscular, subcutaneous, intraocular, intrasynovial, transepithelial including transdermal, ophthalmic, sublingual and buccal; topically including ophthalmic, dermal, ocular, rectal and nasal inhalation via insufflation and aerosol and rectal systemic.

The active compound may be orally administered, for example, with an inert diluent or with an assimilable edible carrier, or it may be enclosed in hard or soft shell gelatin capsules, or it may be compressed into tablets, or it may be incorporated directly with the food of the diet. For oral therapeutic administration, the active compound may be incorporated with excipient and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 6% of the weight of the unit. The amount of active compound in such therapeutically useful compositions is such that a suitable dosage will be obtained. Preferred compositions or preparations according to the present invention are prepared so that an oral dosage unit form contains between about 1 and 1000 mg of active compound.

The tablets, troches, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active compound may be incorporated into sustained-release preparations and formulations.

The active compound may also be administered parenterally or intraperitoneally. Solutions of the active compound as a free base or pharmacologically acceptable salt can be prepared in water suitably mixed with a surfactant such as hydroxypropylcellulose. Dispersion can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the for must be sterile and must be fluid to the extent that easy syringability exists. It may be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and .by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by use of agents delaying absorption, for example, aluminum monostearate and gelatin.

Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze drying technique which yield a powder of the active ingredient plus any additional desired ingredient from previously sterile-filtered solution thereof.

The therapeutic compounds of this invention may be administered to a mammal alone or in combination with pharmaceutically acceptable carriers, as noted above, the proportion of which is determined by the solubility and chemical nature of the compound, chosen route of administration and standard pharmaceutical practice.

The dosage of the present therapeutic agents which will be most suitable for prophylaxis or treatment will vary with the form of administration, the particular compound chosen and the physiological characteristics of the particular patient under treatment. Generally, small dosages will be used initially and if necessary, will be increased by small increments until the optimum effect under the circumstances is reached. The therapeutic human dosage, based on physiological studies using rats, will generally be from about 0.01 mg to about 100 mg/kg of body weight per day or from about 0.4 mg to about 10 g or higher although it may be administered in several different dosage units from once to several times a day. Oral administration requires higher dosages.

We claim:

1. A method for the selective treatment of cell growth and differentiation characterized by activity of the human epidermal growth factor receptor type 2 (HER2) comprising administering to a patient in need of such treatment an HER2 receptor inhibiting effective amount of a compound of the formula:

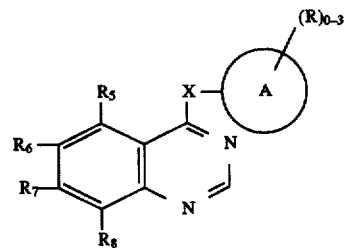

wherein

A is a substituted or unsubstituted monocyclic aryl or heteroaryl ring selected from phenyl, pyrrolyl, thienyl, furyl, thiazolyl, imidazolyl, pyrazolyl, pyridyl, pyrazinyl, pyrimidinyl, pyridazinyl, isothiazolyl, isoxazolyl and oxazolyl;

X is a bond, O, S, SO, $SO_2$, $OCH_2$, $CR_4=CR_4$, $C\equiv C$, $NR_4$ or $NR_4CH_2$;

R independently includes hydrogen, alkyl, phenyl, halophenyl, aralkyl, hydroxy, alkoxy, aryloxy, acyloxy, halo, haloalkyl, amino, mono- and di-alkylamino, acylamino, carboxy, amido, mono- and di-alkylamido, alkylthio, alkylsulfinyl, and alkylsulfonyl;

$R_4$ is hydrogen, alkyl or aralkyl; and $R_5$, $R_6$, $R_7$ and $R_8$ are independently hydrogen, alkoxy or aralkoxy; or a pharmaceutically acceptable salt thereof.

2. A method for the selective treatment of cell growth and differentiation characterized by activity of the human epidermal growth factor receptor type 2 (HER2) comprising administering to a patient in need of such treatment an HER2 receptor inhibiting effective amount of a compound of the formula:

17

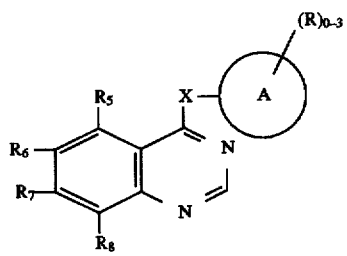

wherein

A is a substituted or unsubstituted bicyclic aryl or heteroaryl ring selected from naphthyl, tetralinyl, 1,2,3,4-tetrahydroquinolinyl, benzofuryl, benzothienyl, indanyl, indolyl, indolinyl, 1,3-benzodioxolyl, benzodioxanyl, quinolinyl, tetrahydroquinolinyl, isoquinolinyl, quinazolinyl and quinoxalinyl.

X is a bond, O, S, SO, $SO_2$, $OCH_2$, $CR_4=CR_4$, $C\equiv C$, $NR_4$ or $NR_4CH_2$;

R independently includes hydrogen, alkyl, phenyl, halophenyl, aralkyl, hydroxy, alkoxy, aryloxy, acyloxy, halo, haloalkyl, amino, mono- and di-alkylamino, acylamino, carboxy, amido, mono- and di-alkylamido, alkylthio, alkylsulfinyl, and alkylsulfonyl;

$R_4$ is hydrogen, alkyl or aralkyl; and $R_5$, $R_6$, $R_7$ and $R_8$ are independently hydrogen, alkoxy or aralkoxy; or a pharmaceutically acceptable salt thereof.

3. A method for the selective treatment of cell growth and differentiation characterized by activity of the human epidermal growth factor receptor type 2 (HER2) comprising administering to a patient in need of such treatment an HER2 receptor inhibiting effective amount of a compound of the formula:

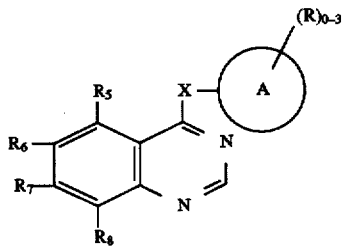

wherein

A is a substituted or unsubstituted monocyclic cycloalkyl or heterocycloalkyl ring selected from cyclopentyl, cyclohexyl, cycloheptyl, decalinyl, piperdinyl, piperazinyl, morpholinyl or decahydroquinolinyl.

X is a bond, O, S, SO, $SO_2$, $OCH_2$, $CR_4=CR_4$, $C\equiv C$, $NR_4$ or $NR_4CH_2$;

R independently includes hydrogen, alkyl, phenyl, halophenyl, aralkyl, hydroxy, alkoxy, aryloxy, acyloxy, halo, haloalkyl, amino, mono- and di-alkylamino, acylamino, carboxy, amido, mono- and di-alkylamido, alkylthio, alkylsulfinyl, and alkylsulfonyl;

$R_4$ is hydrogen, alkyl or aralkyl; and $R_5$, $R_6$, $R_7$ and $R_8$ are independently hydrogen, alkoxy or aralkoxy; or a pharmaceutically acceptable salt thereof.

4. A method for the selective treatment of cell growth and differentiation characterized by activity of the human epidermal growth factor receptor type 2 (HER2) comprising administering to a patient in need of such treatment an HER2

18 receptor inhibiting effective amount of a compound of the formula:

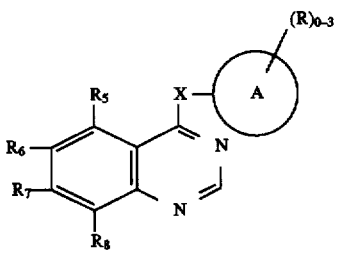

wherein

A is a substituted or unsubstituted bicyclic cycloalkyl or heterocycloalkyl ring selected from decalinyl or decahydroquinolinyl.

X is a bond, O, S, SO, $SO_2$, $OCH_2$, $CR_4=CR_4$, $C\equiv C$, $NR_4$ or $NR_4CH_2$;

R independently includes hydrogen, alkyl, phenyl, halophenyl, aralkyl, hydroxy, alkoxy, aryloxy, acyloxy, halo, haloalkyl, amino, mono- and di-alkylamino, acylamino, carboxy, amido, mono- and di-alkylamido, alkylthio, alkylsulfinyl, and alkylsulfonyl;

$R_4$ is hydrogen, alkyl or aralkyl; and $R_5$, $R_6$, $R_7$ and $R_8$ are independently hydrogen, alkoxy or aralkoxy; or a pharmaceutically acceptable salt thereof.

5. A method for the selective treatment of cell growth and differentiation characterized by activity of the human epidermal growth factor receptor type 2 (HER2) comprising administering to a patient in need of such treatment an HER2 receptor inhibiting effective amount of a compound of the formula:

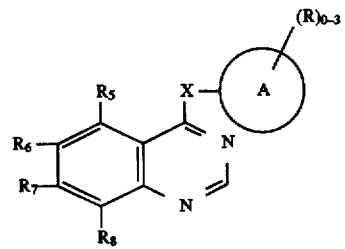

wherein

A is substituted and unsubstituted phenyl, pyridyl, thienyl, furyl, pyrazolyl, naphthyl, tetralinyl, 1,2,3,4-tetrahydroquinolinyl, indanyl, indolyl, indolinyl, quinolinyl, tetrahydroquinolinyl, cyclohexyl, piperdinyl or piperazinyl;

X is a bond, O, S, or $NR_4$;

R is hydrogen, alkyl, alkoxy, halo, haloalkyl, alkylthio, alkylsulfinyl, alkylsulfonyl, phenyl and aralkyl;

$R_4$ is hydrogen, alkyl or aralkyl; and $R_5$, $R_6$, $R_7$, and $R_8$ are independently hydrogen or alkoxy; or a pharmaceutically acceptable salt thereof.

6. A method for the selective treatment of cell growth and differentiation characterized by activity of the human epidermal growth factor receptor type 2 (HER2) comprising administering to a patient in need of such treatment an HER2 receptor inhibiting effective amount of a compound of the formula:

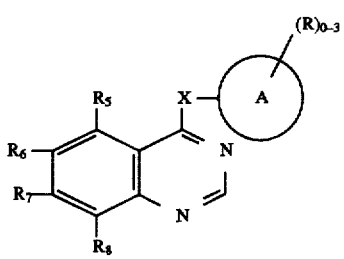

wherein

A is substituted and unsubstituted phenyl, naphthyl or indolyl;

X is a bond;

R is hydrogen, methoxy, ethoxy, chloro, trifluoromethyl, methylsulfonyl, phenyl and benzyl;

$R_4$ is hydrogen, methyl or benzyl; and $R_5$, $R_6$, $R_7$, and $R_8$ are independently hydrogen or methoxy; or a pharmaceutically acceptable salt thereof.

7. A method according to claim 1 where the compound administered is 4-(2-phenylethylenyl)-6,7-dimethoxyquinazoline or a pharmaceutically acceptable thereof.

8. A method according to claim 2 where said compound administered is 6,7-dimethoxy-4-naphthalen-1yl-ethynylquinazoline or a pharmaceutically acceptable thereof.

9. A method according to claim 5 where said compound administered is selected from:

4-(2-methoxypyridin-5-yl)-6,7-dimethoxyquinazoline, 4-(4-phenylpiperidin-1-yl)-6,7-dimethoxyquinazoline, 4-[4-(3-chlorophenyl)piperazin-1-yl]-6,7-dimethoxyquinazoline and 4-(1,2,3,4-tetrahydroquinolin-1-yl)-6,7-dimethoxyquinazoline or a pharmaceutically acceptable thereof.

10. A method according to claim 5 where said compound administered is selected from:

6,7-dimethoxy-4-(β-naphthylamino)quinazoline,

4-[N-(5-indanyl)amino]-6,7-dimethoxyquinazoline,

N-benzyl-N-(6,7-dimethoxyquinazolin-4-yl)-N-phenylamine, 6,7-dimethoxy-4-(N-methylanilino) quinazoline, N-(3-chlorophenyl)-N-(6,7-dimethoxyquinazolin-4-yl)-N-methylamine, 4-(3-aminopyrazolyl)-6,7-dimethoxyquinazoline and 4-(cyclohexylanilino)-6,7-dimethoxyquinazoline or a pharmaceutically acceptable thereof.

11. A method according to claim 5 where the compound administered is 6,7-dimethoxy-4-(α-naphthylamino)quinazoline or a pharmaceutically acceptable salt thereof.

12. A method according to claim 6 where said compound administered is selected from:

4-(naphthalen-1-yl)-6,7-dimethoxyquinazoline, 4-(naphthalen-2-yl)-6,7-dimethoxyquinazoline, 4-(3-phenylphenyl)-6,7-dimethoxyquinazoline, 4-(indol-3-yl)-6,7-dimethoxyquinazoline and 4-(1-methylindol-3-yl)-6,7-dimethoxyquinazoline or a pharmaceutically acceptable salt thereof.

13. A method according to claim 6 where the compound administered is 4-(1-benzylindol-3-yl)-6,7-dimethoxyquinazoline or a pharmaceutically acceptable salt thereof.

* * * * *

UNITED STATES PATENT AND TRADEMARK OFFICE
CERTIFICATE OF CORRECTION

PATENT NO. : 5,721,237
DATED : February 24, 1998
INVENTOR(S) : Michael R. Myers; Alfred P. Spada; Martin P. Maguire; Paul E. Persons It is certified that error appears in the above-identified patent and that said Letters Patent is hereby corrected as shown below:

```
Title page, item [*]
```
    Notice: The term of this patent shall not extend beyond the expiration date of Pat. No. 08/229,886

```
Item [45]
```
    Date of Patent: *Feb. 24, 1998

Signed and Sealed this

Fifteenth Day of September, 1998

BRUCE LEHMAN

*Attest:*

*Attesting Officer*    *Commissioner of Patents and Trademarks*